(12) United States Patent
Roby et al.

(10) Patent No.: US 6,527,749 B1
(45) Date of Patent: Mar. 4, 2003

(54) TWO COMPONENT DISPENSER SYSTEM

(75) Inventors: Mark S. Roby, Kilingworth, CT (US); Ernie Aranyi, Easton, CT (US); Richard Yagami, Ridgefield, CT (US); H. Jonathan Tovey, Monroe, CT (US)

(73) Assignee: United States Surgical Corporation, Norwalk, CT (US)

(*) Notice: Subject to any disclaimer, the term of this patent is extended or adjusted under 35 U.S.C. 154(b) by 166 days.

(21) Appl. No.: 09/595,961

(22) Filed: Jun. 19, 2000

Related U.S. Application Data (60) Provisional application No. 60/068,220, filed on Dec. 19, 1997, and provisional application No. 60/068,218, filed on Dec. 19, 1997.

(51) Int. Cl.[7] ............................................. A61M 5/00
(52) U.S. Cl. ..................... 604/191; 604/187; 604/218; 604/220; 604/257; 604/258
(58) Field of Search .................... 604/191, 187, 604/218, 220, 257, 258; 222/214, 145, 135, 136, 185, 182, 212, 450

(56) References Cited

U.S. PATENT DOCUMENTS

| | | |
|---|---|---|
| 1,948,388 A | 2/1934 | Liberson |
| 2,112,160 A | 3/1938 | Johnson |
| 3,223,083 A | 12/1965 | Cobey |
| 3,236,418 A | 2/1966 | Dalle et al. |
| 3,467,096 A | 9/1969 | Horn |
| 3,521,792 A * | 7/1970 | Davidson .................... 222/136 |
| 3,767,085 A | 10/1973 | Cannon et al. |
| 4,040,420 A | 8/1977 | Speer |
| 4,121,739 A | 10/1978 | Devaney et al. |
| 4,226,235 A | 10/1980 | Sarnoff et al. |
| 4,260,077 A | 4/1981 | Schroeder |
| 4,359,049 A | 11/1982 | Redl et al. |
| 4,465,479 A | 8/1984 | Gahwiler |
| 4,631,055 A | 12/1986 | Redl et al. |
| 4,673,395 A | 6/1987 | Phillips |
| 4,734,261 A | 3/1988 | Koizumi et al. |
| 4,735,616 A | 4/1988 | Eibl et al. |
| 4,773,562 A * | 9/1988 | Gueret ....................... 222/135 |
| 4,801,465 A * | 1/1989 | Sponer ....................... 222/136 |
| 4,826,048 A | 5/1989 | Skorka et al. |
| 4,874,368 A | 10/1989 | Miller et al. |
| 4,902,281 A | 2/1990 | Avoy |
| 4,913,316 A * | 4/1990 | Richter ....................... 222/136 |
| 4,978,336 A | 12/1990 | Capozzi et al. |
| 4,979,942 A | 12/1990 | Wolf et al. |
| 5,049,135 A * | 9/1991 | Davis ......................... 604/181 |
| 5,116,316 A | 5/1992 | Capozzi et al. |
| 5,226,877 A | 7/1993 | Epstein |
| 5,255,823 A * | 10/1993 | Tichy et al. ................. 222/153 |
| 5,290,259 A | 3/1994 | Fischer |

(List continued on next page.)

Primary Examiner—Thomas Denion
Assistant Examiner—Theresa Trieu (57) ABSTRACT

An applicator is provided for dispensing a first and a second protein solution to form a biological adhesive where the solutions can be deflected by a deflection assembly during dispensing for the adhesive to cover a broad or limited area. The applicator includes a housing having a housing head for enclosing therein a first reservoir containing a first component, and a second reservoir containing a second component. The first and second components are preferably fibrinogen and thrombin which intermix with water to form the first and second protein solutions, respectively. The housing further includes an elongated body portion defining a longitudinal axis for enclosing therein a conduit assembly having a first and a second conduit in communication with the first and second reservoir, respectively. The solutions intermix on an application site to form a fibrin sealant. In an alternate embodiment, the applicator includes two valves. A first valve opens and closes the proximal ends of two conduit assemblies for introducing water or other substance to the reservoirs. A second valve opens and closes the distal ends of the two conduit assemblies to permit and prevent the dispensing of the protein solutions.

37 Claims, 7 Drawing Sheets

U.S. PATENT DOCUMENTS

| | | | |
|---|---|---|---|
| 5,328,462 A | * 7/1994 | Fischer | 604/82 |
| 5,332,157 A | * 7/1994 | Proctor | 222/136 |
| 5,368,563 A | 11/1994 | Lonneman et al. | |
| 5,409,465 A | 4/1995 | Boggs et al. | |
| 5,464,396 A | 11/1995 | Barta et al. | |
| 5,474,540 A | 12/1995 | Miller et al. | |
| 5,505,704 A | 4/1996 | Pawelka et al. | |
| 5,520,658 A | 5/1996 | Holm | |
| 5,582,596 A | 12/1996 | Fukunaga et al. | |
| 5,582,896 A | 12/1996 | Fukunaga et al. | |
| 5,643,206 A | 7/1997 | Fischer | |
| 5,656,035 A | * 8/1997 | Avoy | 604/191 |
| 5,740,965 A | 4/1998 | Miyagi et al. | |
| 5,759,169 A | * 6/1998 | Mars | 604/191 |
| 5,901,883 A | * 5/1999 | Ritsche | 222/137 |
| 6,036,057 A | * 3/2000 | Poutiatine | 222/137 |
| 6,047,861 A | * 4/2000 | Vidal et al. | 222/137 |
| 6,165,201 A | * 12/2000 | Sawhney et al. | 606/214 |
| 6,274,090 B1 | * 8/2001 | Coedho et al. | 422/101 |

\* cited by examiner

TWO COMPONENT DISPENSER SYSTEM

PRIORITY

This application claims priority to a U.S. Provisional Application filed on Dec. 19, 1997 by Roby et al. having U.S Provisional Application Serial No. 60/068,218, the contents of which are hereby incorporated by reference. This application also claims priority to a U.S. Provisional Application filed on Dec. 19, 1997 by Roby et al. having U.S. Provisional Application Serial No. 60/068,220, the contents of which are hereby incorporated by reference.

BACKGROUND

1. Technical Field

The disclosure relates generally to an applicator for applying a tissue sealant based on human or animal proteins and more particularly to an apparatus for applying an adhesive formed by combining solutions of the proteins to tissues or organs for sealing wounds, stopping bleeding and the like.

2. Description of Related Art

A fibrin sealant is a biological adhesive formed by mixing two protein components, namely, fibrinogen and thrombin. Each protein component is derived from human plasma and is subjected to virus elimination procedures. The components are typically individually dehydrated and stored in separate vials as sterile freeze-dried powders.

It is known that purified fibrinogen and thrombin, together with a variety of known adjuvants, can be combined in vitro to produce a polymer having great potential benefit, both as a hemostatic agent and as a tissue adhesive. Because of the rapid polymerization upon intimate interaction of fibrinogen and thrombin, it is important to maintain these two blood proteins separate until applied at the application site. These protein solutions are generally delivered by devices such as a dual syringe apparatus. One dual syringe apparatus for applying a fibrinogen-based tissue adhesive is disclosed in U.S. Pat. No. 4,359,049 to Redl et al. Redl et al. disclose a mechanism in which two standardized one-way syringes are held in a support having a common actuating means. The dispensing end of each syringe is inserted into a collection manifold where the two components are mixed. The components are then dispensed through a common needle capable of covering a limited area of the application site.

However, it is sometimes desirable or necessary to cover a broad area of a wound, either to stop bleeding, to fix tissue or to prevent infection and sometimes it is desirable to cover a limited area. It is also desirable to prevent the two components from mixing within the dispensing device.

Further, all known devices for dispensing solutions of fibrinogen and thrombin require the addition of these proteins in powdered form to the body of the syringe. This makes the proteins susceptible to contamination by impurities which may enter the syringe body. Further still, the use of the syringe body to mix the proteins with water to create the protein solutions can cause the solutions to leak out from either the dispensing end of each syringe or the proximal end of the syringe body.

Additionally, a dual syringe apparatus for the application of fibrinogen and thrombin solutions to an application site generally contains several parts, such as a syringe plunger, a "Y" manifold connector, a dispensing needle, a syringe holder, syringe needles, and conduits for transporting the solutions to the dispensing needle. Therefore, known fibrin sealant applicators, such as disclosed in U.S. Patent to Redl et al. discussed above, and in U.S. Pat. No. 4,874,368 to Miller et al. and U.S. Pat. No. 4,979,942 to Wolf et al. are difficult to reuse. The replenishment of the protein components typically require removing a clip which couples the syringe plunger, removing the syringe plunger, detaching the syringes from the "Y" connector, removing the syringes from the holder, inserting new syringes, affixing the syringes to the "Y" connector, adding fibrinogen to one syringe and thrombin to another syringe, adding sterile water to each syringe, replacing the syringe plunger, replacing the plunger clip, and mixing the solutions. In an application where time is of the essence, such a lengthy replenishing process is impractical and cumbersome.

SUMMARY

Two applicator embodiments are provided for dispensing a first and a second protein solution to form a biological adhesive. In the first embodiment, the protein solutions can be deflected during dispensing in order for the adhesive to cover a broad area. The applicator includes a housing configured to receive a plurality of reservoirs each having a sealable opening therein; a conduit assembly having a pair of conduits in respective fluid communication with separate of the reservoirs; an activator assembly provided on the housing having an activator moveable from a first position to a second position to pressurize each of the plurality of reservoirs to dispense the biological adhesive components through the pair of conduits to a distal end thereof; and a deflection assembly provided in proximity to the distal end having a deflection member to deflect the biological adhesive components during dispensing.

The first and second components are preferably fibrinogen and thrombin which intermix on an application site to form a fibrin sealant. The deflection assembly includes a deflection member capable of longitudinal movement for blocking and unblocking the solution spray as it is dispensed from the applicator for changing the uniformity of the solutions throughout the application site during dispensing.

In a second embodiment, an applicator is provided for dispensing a first and a second component of a biological adhesive. The applicator includes a housing configured to receive a plurality of collapsible reservoirs and a plurality of vials each having a sealable opening therein; a first conduit assembly having a proximal end configured for respective fluid communication with one of the vials, an intermediate portion made up at least partially by one of the collapsible reservoirs and a distal end configured to be open to the environment; a second conduit assembly having a proximal end configured for respective fluid communication with one of the vials, an intermediate portion made up at least partially by one of the collapsible reservoirs and a distal end configured to be open to the environment; an activator assembly provided on the housing having an activator moveable from a first position to a second position to simultaneously compress each of the plurality of reservoirs to dispense the biological adhesive components through the first and second conduits from respective distal ends thereof; and a valve assembly having a first valve operatively associated with the proximal ends of the first and second conduit assemblies for opening and closing the conduits and a second valve independent of the first valve and operatively associated with the distal ends of the first and second conduit assemblies for opening and closing the conduits adjacent the distal ends.

The housing further includes an elongated body portion defining a longitudinal axis for enclosing a portion of the conduit assemblies therein. An applicator tip having two separate channels in communication with the conduits may be provided on a distal end of the elongated body portion for dispensing the components at the application site. Similarly, to the first embodiment, the first and second components are preferably fibrinogen and thrombin which intermix to form a fibrin sealant.

BRIEF DESCRIPTION OF THE DRAWINGS

Various embodiments are described herein with reference to the drawings, wherein.

DETAILED DESCRIPTION OF PREFERRED EMBODIMENTS

Figures 1, 1A, 1B:
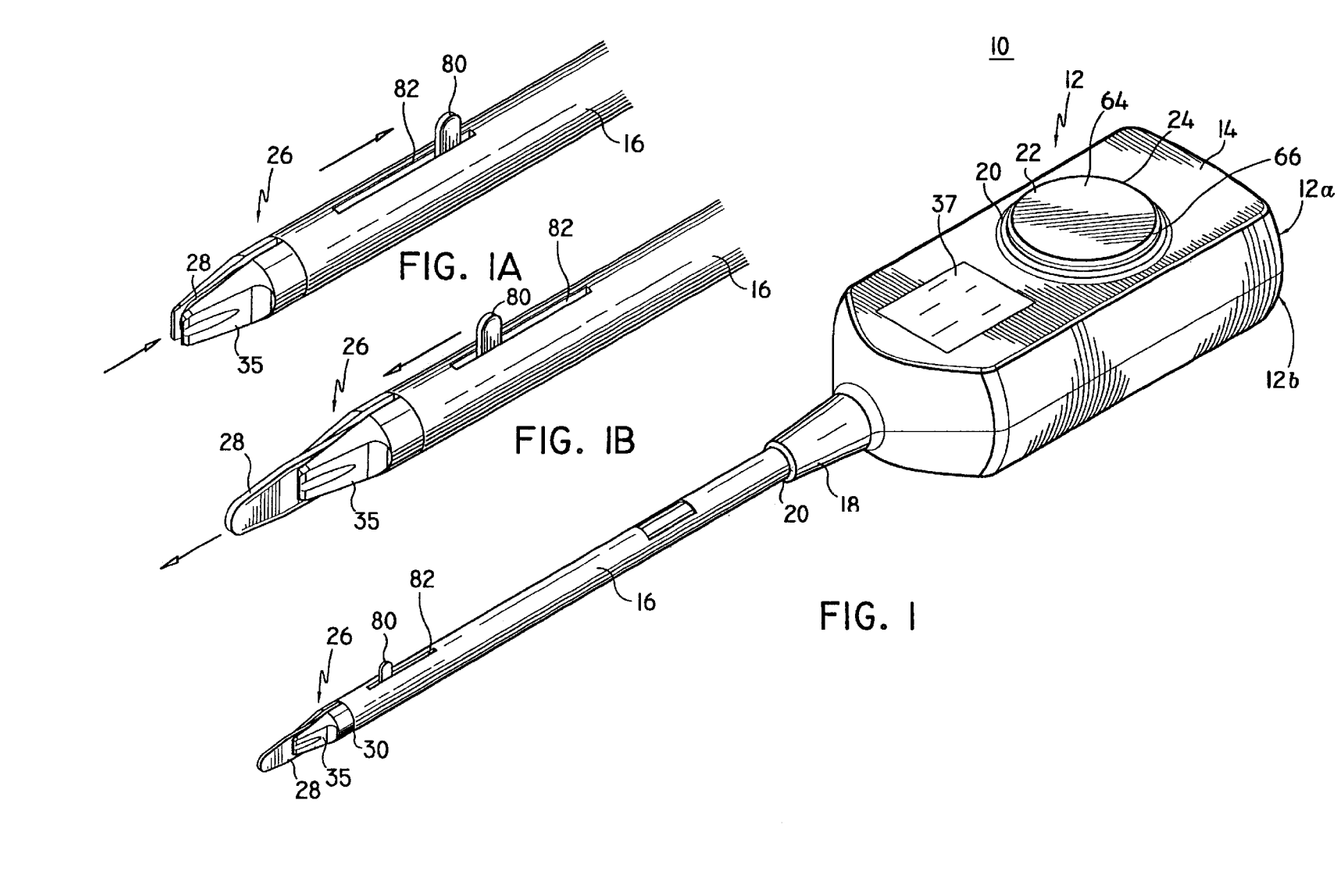
FIG. 1 is a perspective view of an embodiment of a fibrin sealant applicator having a deflection assembly in accordance with the present disclosure.
FIG. 1A is an enlarged perspective view of a distal end of the fibrin sealant applicator of the embodiment of FIG. 1 with a control lever of the deflection assembly in a retracted position.
FIG. 1B is an enlarged perspective view of a distal end of the fibrin sealant applicator of the embodiment of FIG. 1 with the control lever of the deflection assembly in an advanced position.

Referring to FIG. 1, a fibrin sealant applicator according to a first embodiment of the present disclosure is shown. The applicator is designated generally by numeral 10 and includes a housing 12 having a housing head 14 and an elongated body portion 16 defining a longitudinal axis. Housing head 14 contains a conically-shaped distal end 18 having a bore 20 in the center thereof dimensioned to receive body portion 16. While housing head 14 is shown as being rectangular, it is understood that other shapes that contribute to the case of gripping and controlling the applicator 10 may be used.

Opening 20 is configured for receiving an activator assembly 22 having an activator 24 for effectuating the dispensing of biological components as further described below. A deflection assembly 26 is provided having a deflection member 28 at a distal end 30 of body portion 16. Deflection assembly 26 provides longitudinal movement of deflection member 28 to effectuate various dispensing methods of the biological components, such as spraying and dripping as discussed below. FIG. 1A shows deflection member 28 in the retracted position and FIG. 1B shows deflection member 28 in the advanced position. Deflection member 28 is preferably manufactured from a non-stick material such as PTFE.

In a preferred embodiment, the biological components are a fibrinogen solution and a thrombin solution which intermix to form a fibrin sealant. It is to be understood, however, that other biological fluids may be substituted, depending upon the choice of mixture that is to be dispensed.

Figures 2, 2A, 2B:
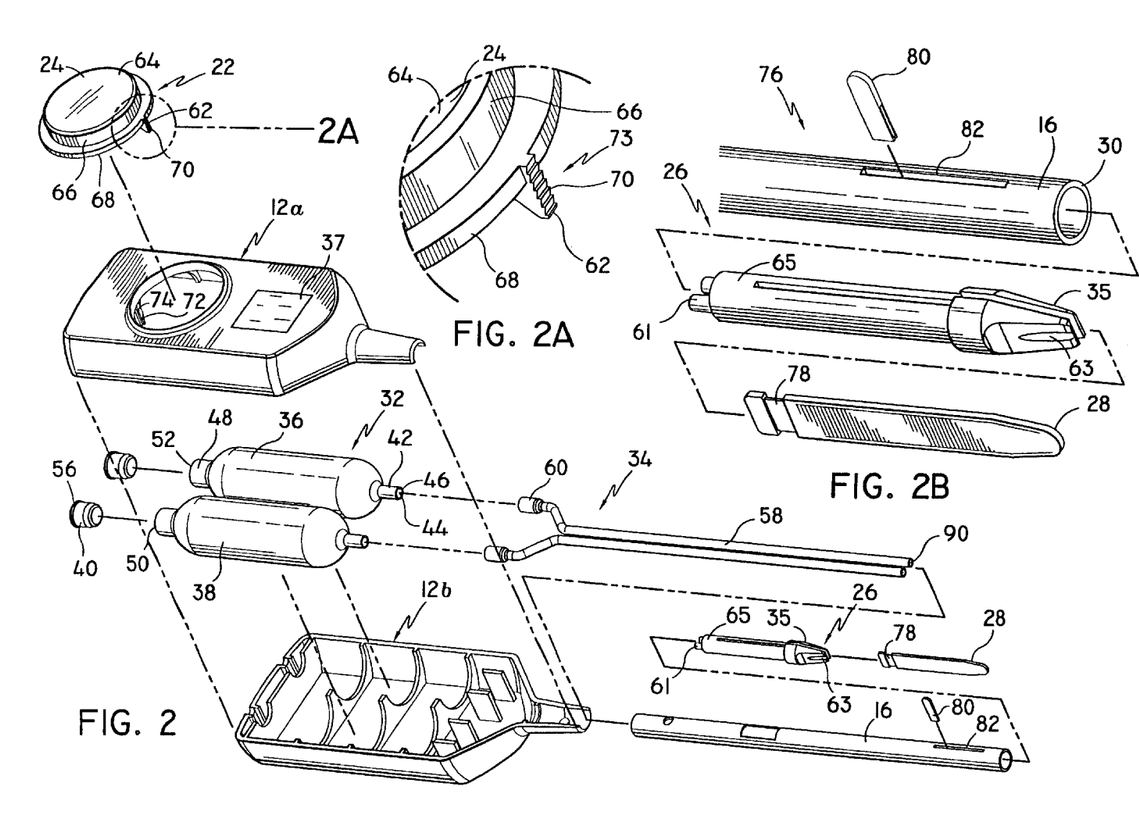
FIG. 2 is a perspective exploded view of the embodiment of FIG. 1.
FIG. 2A is an enlarged view of a ratchet member on an activator assembly shown by FIG. 1.
FIG. 2B is an enlarged view of the distal end of the fibrin sealant applicator illustrating the assembly of the deflection assembly to the embodiment of FIG. 1.
Figure 2C:
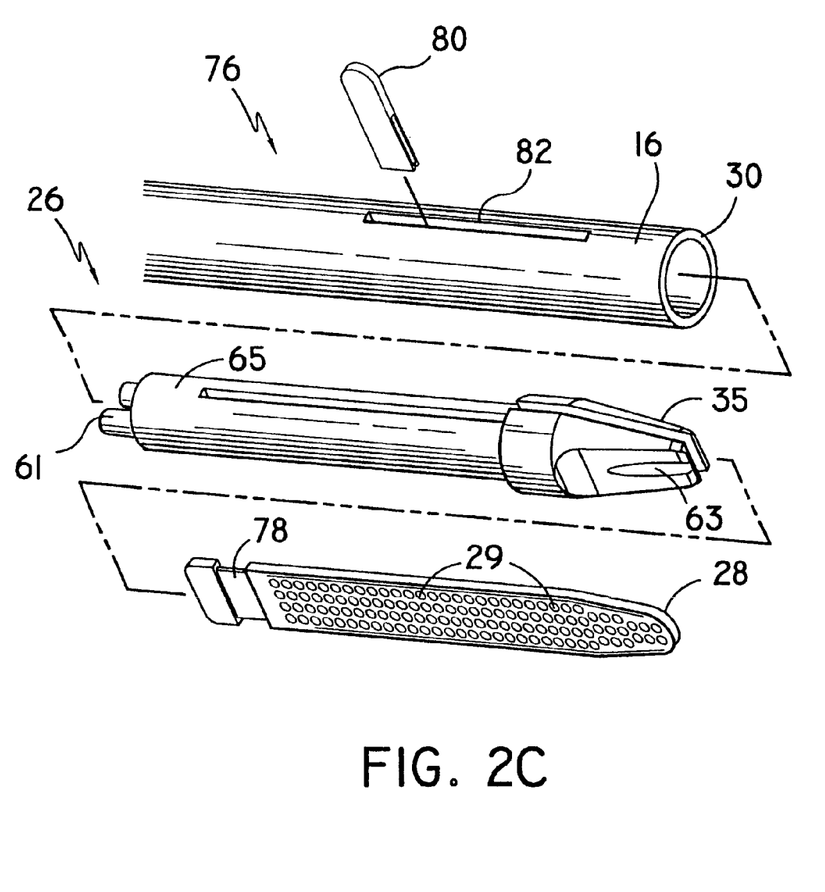
FIG. 2C is an enlarged view of the distal end of the fibrin sealant applicator illustrating the assembly of an alternative embodiment of the deflection assembly.

The internal components of housing 12 will now be discussed in detail with reference to FIGS. 2–2C. As shown in FIG. 2, housing 12 is formed from molded housing half sections 12a and 12b which are formed with internal partitions configured to properly align the internal components of applicator 10 with respect to each other and to prevent movement of the components. The internal components of applicator 10 include a reservoir assembly 32 and a conduit assembly 34. The two assemblies are interrelated with each other and with activator assembly 22 and deflection assembly 26 discussed above.

Reservoir assembly 32 includes first and second reservoirs 36, 38 and two plugs 40. First reservoir 36 and second reservoir 38 are preferably constructed from a flexible material and contain the first and second biological components, respectively. First and second reservoirs 36, 38 are identical for encasing an equal is volumetric amount of their respective protein solution as compared to the other reservoir. It is contemplated to provide a different color for each reservoir to easily recognize the reservoir containing fibrinogen and the reservoir containing thrombin. It is further contemplated to provide a different shape for each reservoir for the same purpose. However, the volumetric amount stored within first reservoir 36 should be equal to the volumetric amount stored within second reservoir 38 to maintain a pre-determined fibrinogen to thrombin solution ratio, which is typically a 1:1 ratio.

It is still further contemplated that first and second reservoirs 36, 38 are manufactured from a transparent plastic for being able to view the amount of solution and to determine if the solution has been sufficiently intermixed before being dispensed on the application site. It is further contemplated to provide calibration markings on first and second reservoirs 36, 38. It is additionally contemplated that reservoir assembly 32 is permanently affixed to conduit assembly 34. In such an embodiment, reservoir assembly 32 and conduit assembly 34 can be disposed of after each use and new reservoir and conduit assemblies can be fitted to applicator 10. A window 37 on housing half-section 12a will also permit a user to view the contents within first and second reservoirs 36, 38.

First and second reservoirs 36, 38 include a first cylindrical extension 42 having a center throughbore 44 at a distal end 46, a second cylindrical extension 48 having a central throughbore 50 at a proximal end 52. Central throughbore 50 is used for placing the biological components in reservoirs 36, 38. Plug 40 is used to vacuum seal central throughbore 50 to prevent contamination of the biological components. Plug 40 includes a silicon surface 56 capable of being penetrated by a syringe needle for adding a liquid, preferably sterile water, within reservoirs 36, 38 to intermix with the biological components to form protein solutions. The protein solutions are kept separated to prevent intermixing and the creation of a fibrin sealant within applicator 10. Upon exertion of pressure on activator 24, the components are forced through conduit assembly 34 to applicator tip 35. The addition of water within reservoirs 36, 38 and the dispensing of protein solutions on the application site are further discussed below.

Although one embodiment for the reservoirs has been illustrated and described, it is to be understood that applicator 10 could be fitted with any of a number of different reservoirs, including, without limitation, syringes, bags or tubing. Furthermore, although the preferred embodiment for reservoir assembly 32 has but two reservoirs, it is to be understood that additional reservoirs containing other solutions can be incorporated within applicator 10.

Conduit assembly 34 includes two conduits 58 each having a nozzle 60 for matingly engaging cylindrical extension 42 on first and second reservoirs 36, 38 for connecting conduit assembly 34 to reservoir assembly 32. Conduit assembly 34 is mounted within housing 12. Two applicator nozzles 61 are press fitted to distal end surface 90 of conduits 58 for dispensing the protein solutions therefrom. Nozzles 61 lead to corresponding dispensing nozzles 63 on applicator tip 35 for dispensing the components in a spray-like manner. Applicator tip 35 is preferably manufactured from a non-stick material such as PTFE. A tubular extension 65 is provided to applicator tip for press fitting to body portion 16.

FIG. 2A is an enlarged view of a portion of activator assembly 22. As described in greater detail below, activator assembly 22 controls the pressure exerted on reservoirs 36, 38, and includes activator 24 and a ratchet member 62. Activator 24 includes an activation area 64, a shaft 66, and a disc 68. Shaft 66 connects activation area 64 with disc 68. Ratchet member 62 extends downwardly from disc 68 and includes teeth 70 for engaging teeth 72 on an inner extension 74 of housing 12 to form structure for controlling the position of activator 24. The control structure is a ratchet mechanism 73. Ratchet member 62 is preferably formed integral with disc 68. Activator 24 may be formed with a transparent material or with a transparent window therein to permit viewing of the internal components of applicator 10.

Deflection assembly 26, as mentioned above includes deflection member 28, and a longitudinal advancement mechanism 76 having a control rod 78 operatively associated with a control lever 80 to distally advance and proximally retract deflection member 28 as control lever 80 is moved along slot 82. It is contemplated to provide a plurality of locking positions to deflection member 28 along control rod 78 for changing the length of deflection member 28 extending beyond applicator tip 35. FIG. 2B is an enlarged view of deflection member 29 showing its connection to control lever 80. FIG. 2C is an enlarged view of an alternative deflection member 28 having a plurality of holes 29 for intermixing the two protein solutions before they are dispensed on the application site.

Figure 3:
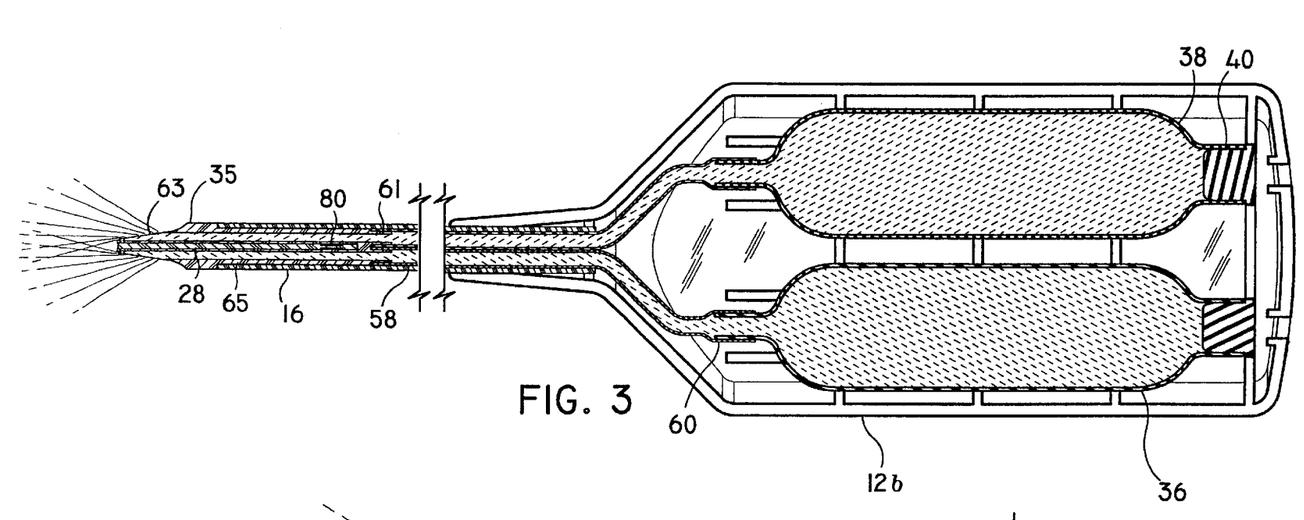
FIG. 3 is a cross-sectional view of the fibrin sealant applicator with a deflection member of the deflection assembly in a retracted position.
Figure 4:
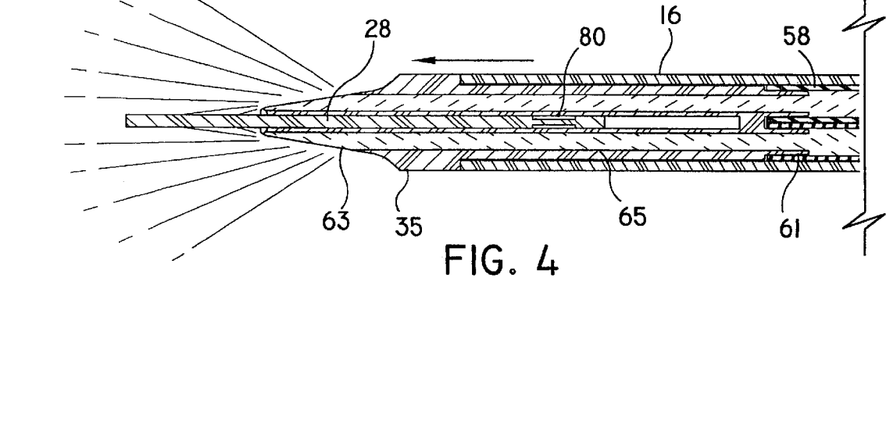
FIG. 4 is a cross-sectional view of the distal end of the fibrin sealant applicator with the deflection member of the deflection assembly in an advanced position.

The operation of applicator 10 with particular attention to changing the amount of area covered by the dispensed adhesive will now be described in detail with reference to FIGS. 3 and 4. As described in commonly owned, co-pending U.S. patent application Ser. No. 08/792,535, the solutions are dispensed by exerting pressure to activation area 64. This causes ratchet mechanism 73 to guide activator 24 downwardly and to force shaft 66 further into housing 12.

As shaft 66 enters housing 12, ratchet mechanism 73 and disc 68 compress reservoirs 36, 38 to dispense each protein solution via a corresponding nozzle 60 into conduit assembly 34. When ceasing to exert pressure to activation area 64, activator 24 is prevented from returning to the inactivated state by ratchet mechanism 73. As a result air cannot be sucked into reservoirs 36, 38 causing difficulty in further compressing reservoirs 36, 38.

While exerting pressure on activation area 64, control rod 78 can be moved distally and proximally to advance and retract deflection member 28, respectively. Deflection member 28 can also be held in a particular position throughout the dispensing procedure. When deflection member 28 is in the retracted position, as shown by FIG. 3, deflection of the spray is avoided. The solutions are therefore dispensed uniformly throughout the application site. On the other hand, when deflection member 28 is in the advanced position, as shown by FIG. 4, a portion of the spray is deflected. In this configuration, the solutions are preferably caused to drip from deflection member 28 onto the application site. Although the preferred embodiment has been described with a particular activator, conduit and deflection assemblies, it is understood that other similar assemblies may be employed to achieve the same functions.

For example, it is contemplated to provide different diameters for conduits 58 for dispensing the biological components in different ratios. Further, an activator assembly may be provided which uses pressurized gas to dispense the components from the reservoirs.

Figures 5, 6A, 6B:
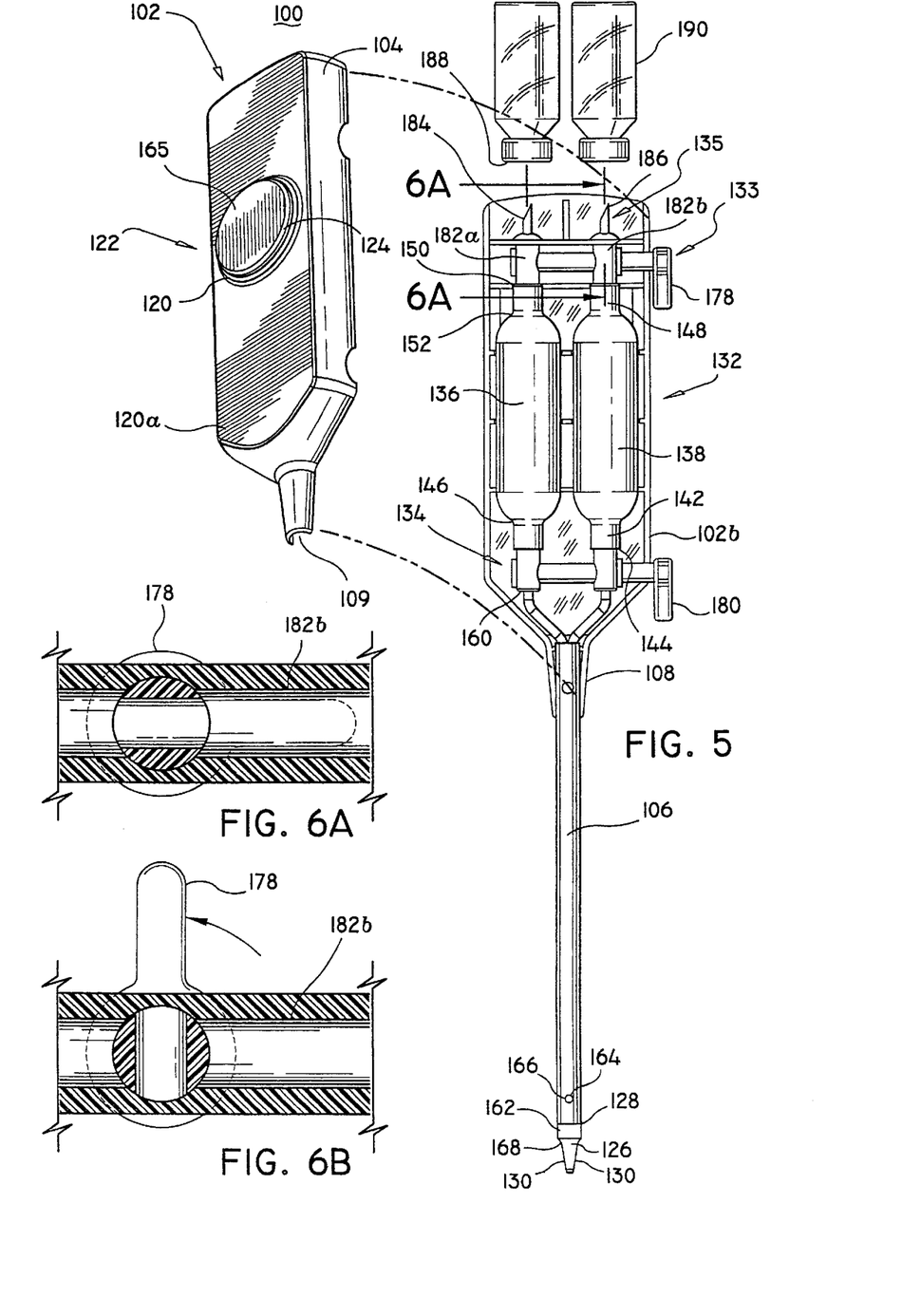
FIG. 5 is a perspective view of an alternative embodiment of a fibrin sealant applicator in accordance with the present disclosure.
FIG. 6A is a cross-sectional view taken along line 6A—6A in FIG. 5 with a first valve in all open position.
FIG. 6B is a cross-sectional view taken along line 6A—6A in FIG. 5 with the first valve in an closed position.

Referring to FIG. 5, a fibrin sealant applicator according to a second embodiment of the present disclosure is shown. The presently disclosed applicator, designated generally by numeral 100, includes a housing 102 having a housing head 104 and an elongated body portion 106 defining a longitudinal axis. Housing head 104 contains a conically-shaped distal end 108 defining a bore 109 in the center thereof dimensioned to receive body portion 106. While housing head 104 is shown as being rectangular, it is understood that other shapes that contribute to the ease of gripping and controlling applicator 100 may be used.

Housing head 104 includes an opening 120 for receiving an activator assembly 122 having an activator 124 for effectuating the dispensing of biological components as further described below. An applicator tip 126 is provided at a distal end 128 of body portion 106 having two boresights 130 for dispensing biological components contained within housing head 104. As in the first embodiment, the biological components are a fibrinogen solution and a thrombin solution which intermix to form a fibrin sealant. It is to be understood, however, that other biological fluids may be substituted, depending upon the choice of mixture that is to be dispensed. Further, applicator tip 126 is preferably manufactured from a non-stick material such as PTFE.

The internal components of housing 102 will now be discussed in detail. As shown in FIG. 5, housing 102 is formed from molded housing half sections 102a and 102b which are formed with internal partitions configured to properly align the internal components of applicator 100 with respect to each other and to prevent movement of the components. The internal components of applicator 100 include a reservoir assembly 132, a valve assembly 133, a first conduit assembly 134, and a second conduit assembly 135. The four assemblies are interrelated with each other and with activator assembly 122 discussed above. For example, an intermediate portion of first and second conduit assemblies 134, 135 is made up at least partially by reservoir assembly 132.

Reservoir assembly 132 includes first and second reservoirs 136, 138. First reservoir 136 and second reservoir 138 are preferably constructed from a flexible material and contain the first and second biological components, respectively. It is contemplated to provide a window on housing half-section 102a to permit a user to view the contents within first and second reservoirs 136, 138 (see, e.g., FIG. 1).

First and second reservoirs 136, 138 include a first cylindrical extension 142 having a central throughbore 144 at a distal end 146, a second cylindrical extension 148 having a central throughbore 150 at a proximal end 152. Central throughbore 144 and central throughbore 150 of each respective reservoir are in alignment with corresponding first and second conduit assemblies 134, 135. Central throughbore 150 is used for placing the biological components in reservoirs 136, 138. Each conduit assembly includes a nozzle 160 at its intermediate portion for connecting to reservoirs 136, 138 via valve assembly 133.

A plug or scalable opening is preferably used to vacuum seal central throughbore 150 to prevent contamination of the biological components, similarly to reservoirs 36, 38. A piercer (not shown) within central throughbore 150 is used to pierce the plug when reservoirs 136, 138 are placed within housing 102. Alternatively, reservoirs 136, 138 having the protein components therein are welded to the proximal ends of first and second conduit assemblies 133, 134 during manufacturing.

Applicator tip 126 includes a cylindrical proximal end 162 and an applicator head 168. Cylindrical proximal end 162 is press fitted to the distal end of elongated body portion 106 to provide communication between boresights 130 and conduit assemblies 134, 135. Each boresight 130 extends through applicator tip 126 to a respective conduit assembly for dispensing the protein solutions to the application site. Cylindrical proximal end 162 includes a clasping button 164 for matingly engaging a hole 166 in body portion 106 to secure applicator tip 126 to elongated body portion 106.

Activator assembly 122 controls the pressure exerted on reservoirs 136, 138, as further described below. Activator 124 may be formed with a transparent material or with a transparent window therein to permit viewing of the internal components of applicator 100.

First and second reservoirs 136, 138 of reservoir assembly 132 are preferably identical for encasing an equal volumetric amount of their respective protein solution. Further, it is contemplated, for example, to provide a different color for each reservoir to easily recognize the reservoir containing fibrinogen and the reservoir containing thrombin. Further still, it is contemplated to provide a different shape for each reservoir for the same purpose. However, the volumetric amount stored within first reservoir 136 should be equal to the volumetric amount stored within second reservoir 138 to maintain a pre-determined fibrinogen to thrombin solution ratio, which is typically a 1:1 ratio.

Valve assembly 133 includes first and second valves 178, 180. First valve 178 is operatively associated with the proximal ends of conduit assemblies 134, 135, which include pathways 182a, 182b. Second valve 180 is operatively associated with the intermediate portion of the conduit assemblies 134, 135. Pathways 182a, 182b lead to first and second reservoirs 136, 138 from first and second piercers 184, 186, respectively. First valve 178 opens and closes the two pathways 182a, 182b. As shown by FIG. 6A, when valve 178 is in the open position, pathway 182b is fully open to permit material to pass therethrough. When first valve 178 is in the closed position, as shown by FIG. 6B, pathway 182b is closed to prevent material to pass therethrough. The same operating mechanism is included for valve 180. The operating mechanism is a type of turnkey operation, which opens and closes first and second valves 178, 180 as it is turned clockwise and counter-clockwise respectively.

Piercers 184, 186 are used to pierce a silicon surface 188 provided on vials 190. Vials 190 dispense sterile water within reservoirs 136, 138 for intermixing with the protein components therein to create protein solutions. The protein components may also be dispensed within reservoirs 136, 138 via vials similar to vials 190 or the like.

During the dispensing of sterile water within reservoirs 136, 138 to intermix with the protein components therein, first valve 178 is kept at an open position to keep pathways 182a, 182b open. Second valve 180 is kept at a closed position to is prevent premature dispensing of the solutions via the distal ends of conduit assemblies 134, 135. When the protein solutions are ready to be dispensed, first valve 178 is at a closed position and second valve 180 is at an open position.

Figure 7A:
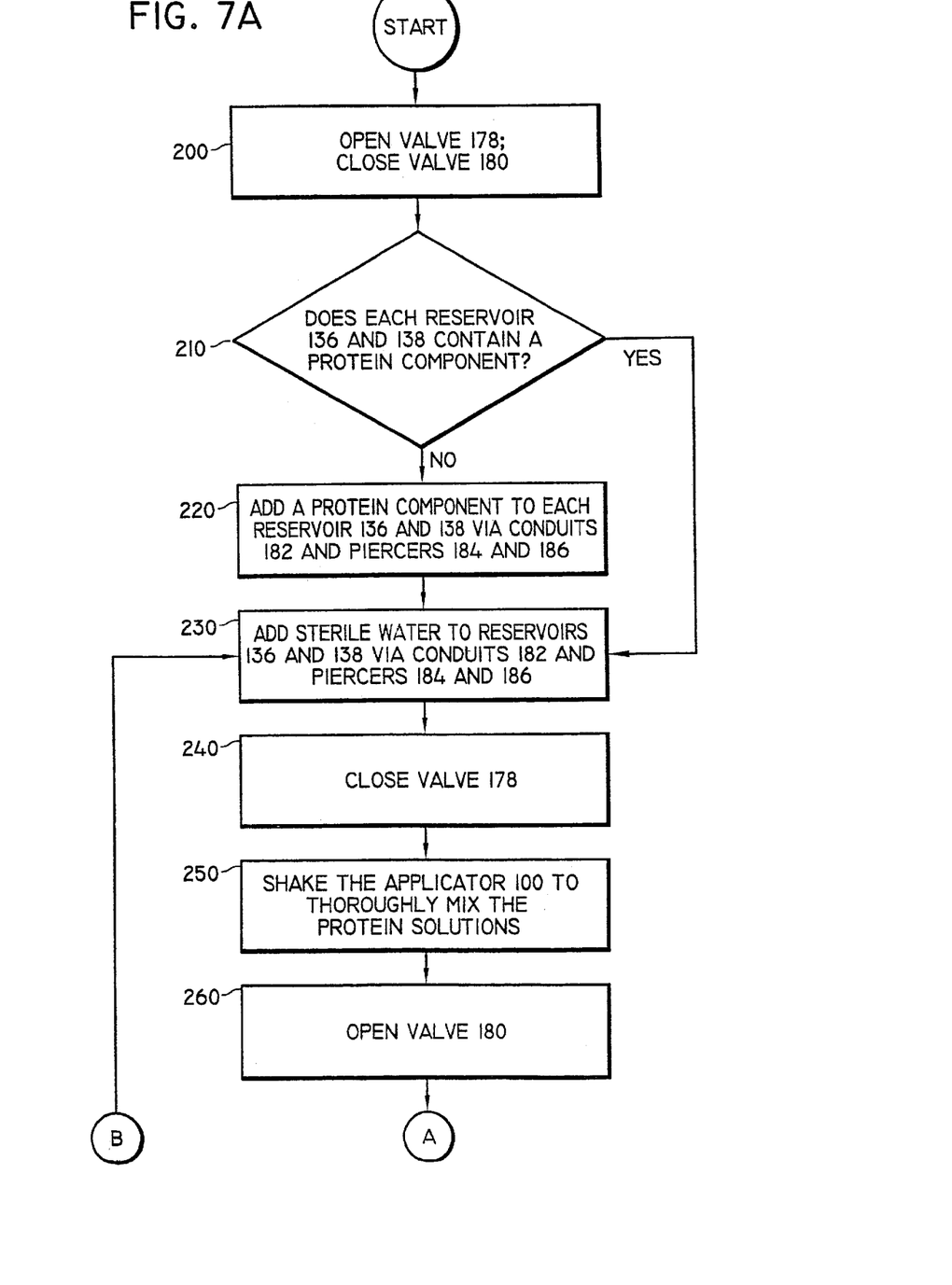
FIGS. 7A and 7B are flow charts depicting the method of use of the fibrin sealant applicator of FIG. 5.
Figure 7B:
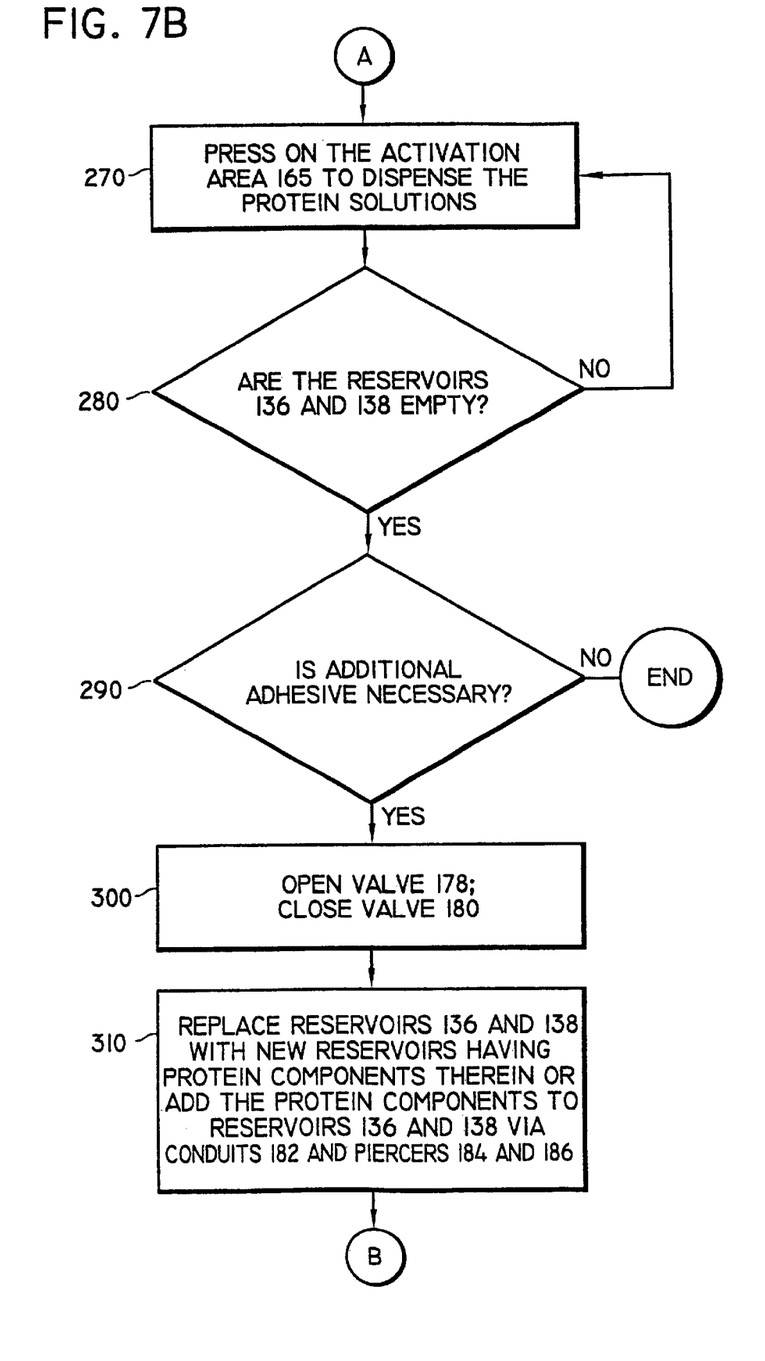

The above methodology will become more apparent with the following detailed description of the operation of applicator 100 with reference to FIGS. 7A and 7B. FIGS. 7A and 7B are flow chart diagrams depicting the operational steps of applicator 100. First, valve 178 is opened and valve 180 is closed (Block 200). If each reservoir 136, 138 contains a protein component (Block 210) the process continues with Block 230. Otherwise, a protein component is added to each reservoir 136, 138 via pathways 182a, 182b of conduit assemblies 134, 135 and pierces 184, 186 (Block 220). Sterile water is then added to reservoirs 136, 138 (Block 230). First valve 178 is then closed (Block 240). Applicator 100 is then shaken to thoroughly mix the components with the sterile water to form protein solutions (Block 250). Second valve 180 is then opened (Block 260).

Before dispensing the protein solutions, activator 124 is maintained in the inactivated state by a ratchet mechanism (similar to FIG. 2A) which has teeth for lockingly engaging teeth on an inner extension of housing 102. Activator 124 is activated by exerting pressure to activation area 165 (Block 270). This causes the ratchet mechanism to guide activator 124 downwardly into housing 102. As activator 124 enters housing 102, it compresses or pressurizes reservoirs 136, 138 to dispense the protein solutions via nozzles 160 located at the intermediate portion of conduit assemblies 135, 135 towards elongated body portion 106.

When ceasing to exert pressure to activation area 165, activator 124 is prevented from returning to the inactivated state by the ratchet mechanism. As a result air cannot be sucked into reservoirs 136, 138 causing difficulty in further compressing reservoirs 136, 138, as described above with respect to the first embodiment of the applicator. Further, the position of activator 124 with respect to housing half-section 102a provides a reference as to the amount of solution remaining in first and second reservoirs 136, 138. For example, when activator 124 is in a fully activated state, there is a small amount of solution left in first and second reservoirs 136, 138. In Block 280, the operator checks, e.g., via a window on having half-section 102a (see, e.g., FIG. 1), to determine if reservoirs 136, 138 are empty. If reservoirs 136, 138 are not empty, continued pressure on activation area 165 will dispense the remaining protein solutions. However, if reservoirs 136, 138 are empty, the operator can check to determine if additional adhesive is necessary (Block 290). If not, the process ends.

If additional adhesive is required, a replenishment process is initiated. First valve 178 is opened and second valve 180 is closed. (Block 300). Reservoirs 136, 138 can then be replaced or protein components may be added to reservoirs 136, 138 via pathways 182 and piercers 184, 186 (Block 310). The process then returns to Block 230 and is repeated.

Although the embodiments herein have been described with a particular activator assembly, it is understood that other similar assemblies may be employed. For example, an activator assembly may be provided which uses pressurized gas to dispense the components from the reservoirs. It is also contemplated to provide a different conduit assembly, for example, an assembly which has conduits with different diameters for allowing the biological components to be dispensed in different ratios.

Therefore, it is understood that various modifications way be made to the embodiments disclosed herein. For example, while specific preferred embodiments of the deflection, conduit, activator, ratchet and reservoir assemblies, have been described in detail, structures that perform substantially the same function in substantially the same way to achieve substantially the same result can also be used. Also, besides applying a fibrin sealant, the fibrin sealant applicator can be used to preform human or veterinary surgical procedures including applying antiseptics, medication and other similar procedures. Therefore, the above description should not be construed as limiting, but merely as exemplifications of preferred embodiments. Those skilled in the art will envision other modifications within the scope and spirit of the claims appended hereto.

What is claimed is:

1. An applicator for dispensing at least one component of a multicomponent biological adhesive, the applicator comprising:
    a reservoir assembly including a plurality of reservoirs;
    a housing configured to receive the reservoir assembly;
    a conduit assembly having a pair of conduits in respective fluid communication with separate of said reservoirs;
    an activator assembly provided on said housing having an activator moveable from a first position to a second position to compress each of said plurality of reservoirs to dispense said multicomponent biological adhesive through said pair of conduits to a distal end of the housing; and
    a deflection assembly having a deflection member movable between a first position within the housing to a second position whereby the deflection member extends from the distal end of the housing to deflect said multicomponent biological adhesive during dispensing.

2. The applicator of claim 1, wherein said reservoirs are at least partially collapsible.

3. The applicator of claim 1, further comprising a pair of applicator nozzles each being in fluid communication with said distal end of one of said pair of conduits and having a spray assembly for dispensing said multicomponent biological adhesive in spray form.

4. The applicator of claim 1, wherein said activator assembly includes control structure for restricting said activator from returning to said first position after the activator is moved from said first position.

5. The applicator of claim 4, wherein said control structure includes a ratchet mechanism.

6. The applicator of claim 1, wherein said deflection assembly includes a control rod operatively associated with said deflection member to move said deflection member from said retracted position to said extended position as said control rod is moved from a first position to a second position.

7. The applicator of claim 6, wherein said deflection member is unitary with said control rod.

8. The applicator of claim 6, wherein said deflection assembly further includes a control lever operatively associated with said control rod to move said control rod from said first position to said second position.

9. The applicator of claim 1, wherein said deflection member includes a plurality of holes.

10. The applicator of claim 1, wherein said deflection assembly includes a locking member for locking said deflection member in a plurality of positions between said retracted position and said extended position.

11. The applicator of claim 1, wherein when said deflection member is in said retracted position said adhesive is dispensed from said applicator uniformly throughout an application site.

12. The applicator of claim 1, wherein said deflection member is in said extended position said adhesive is dispensed from said applicator non-uniformly throughout an application site.

13. The applicator of claim 1, wherein each of said pair of conduits includes independent distal exits.

14. The applicator of claim 1, wherein said conduit assembly further comprising a first nozzle disposed about a first of said pair of conduits and a second nozzle disposed about a second of said pair of conduits.

15. The applicator of claim 1, wherein said multicomponent biological adhesive includes a first component and a second component, said first component is a thrombin solution and said second component is a fibrinogen solution, whereby said adhesive is a fibrin sealant.

16. The applicator of claim 15, wherein said adhesive comprises a predetermined ratio of said thrombin solution to said fibrinogen solution.

17. The applicator of claim 1, wherein said housing includes a housing head for storing said plurality of reservoirs therein and an elongated body portion extending from said housing head.

18. An applicator for dispensing a first and a second component of biological, adhesive, the applicator comprising:
    a housing having a first dispensing conduit for dispensing the first component and a second dispensing conduit for dispensing the second component independent of the first component;
    an activator assembly in communication with the dispensing conduits and both a first reservoir containing the first component and a second reservoir containing the second component, for exerting pressure on the reservoirs for dispensing the components to the dispensing conduits; and
    a dispensing control assembly operatively associated with said dispensing conduits and having a dispensing member operational between a first position and a second position to change the uniformity of the dispensing of said components throughout an application site during dispensing, wherein at the first position the dispensing member is retracted within the housing and at the second position the dispensing member extends from the housing.

19. The applicator of claim 18, further comprising a pair of applicator nozzles in fluid communication with a distal end of one of said dispensing conduits.

20. The applicator of claim 18, wherein said first component is a thrombin solution and said second component is a fibrinogen solution, whereby said adhesive is a fibrin sealant.

21. An applicator for dispensing a first and second component of a biological adhesive, the applicator comprising:
- a conduit assembly having a pair of conduits;
- a collapsible reservoir assembly having a first reservoir containing the first component and a second reservoir containing the second component, the first reservoir being in communication with a first of said pair of conduits and the second reservoir being in communication with a second of said pair of conduits;
- an activator assembly having an activator for imparting pressure to said first and second reservoirs to effect dispensing of said first and second components to said pair of conduits; and
- a blocking member placed between said pair of conduits and being longitudinally moveable between a first position to permit uniform dispensing of said components and a second position to permit non-uniform dispensing of said components throughout an application site.

22. The applicator of claim 21, wherein the conduit assembly, the reservoir assembly and the blocking member are supported within a single housing.

23. The applicator of claim 21, wherein said first component is a thrombin solution and said second component is a fibrinogen solution, whereby said adhesive is a fibrin sealant.

24. An applicator for dispensing biological adhesive components, the applicator comprising:
- a housing configured to receive a plurality of collapsible reservoirs and a plurality of vials each having a sealable opening therein;
- a first conduit assembly having a proximal end configured for respective fluid communication with one of said vials, an intermediate portion made up at least partially by one of said collapsible reservoirs and a distal end configured to be open to the environment;
- a second conduit assembly having a proximal end configured for respective fluid communication with one of said vials, an intermediate portion made up at least partially by one of said collapsible reservoirs and a distal end configured to be open to the environment;
- an activator assembly provided on said housing having an activator moveable from a first position to a second position to simultaneously compress each of said plurality of reservoirs to dispense said biological adhesive components through said first and second conduit assemblies to respective distal ends thereof; and
- a valve assembly having a first valve operatively associated with the proximal ends of the first and second conduit assemblies for opening and closing said proximal ends of said conduit assemblies and a second valve independent of said first valve and operatively associated with the intermediate portions of the first and second conduit assemblies for opening and closing said intermediate portions of said conduit assemblies.

25. An applicator for dispensing biological adhesive components, the applicator comprising:
- a housing configured to receive a plurality of reservoirs;
- a conduit assembly having a pair of conduits in respective fluid communication with separate of said reservoirs;
- an activator assembly provided on said housing having an activator movable from a first position to a second position for decreasing the volumetric capacity of each of said plurality of reservoirs to dispense said biological adhesive components through said pair of conduits to respective distal ends thereof; and
- a valve operatively associated with said conduit assembly for opening and closing said pair of conduits to permit and prevent the dispensing of said biological adhesive components.

26. The applicator of claim 25, further comprising a valve assembly operatively associated with respective proximal ends of the pair of conduits, said valve assembly opens and closes said proximal ends of said pair of conduits to permit and prevent the introduction of components within said vials to said reservoirs.

27. The applicator of claim 25, further comprising a pair of applicator nozzles each being in fluid communication with said distal end of one of said pair of conduits.

28. The applicator of claim 25, wherein said activator assembly includes control structure for restricting said activator from returning to said first position after the activator is moved from said first position.

29. The applicator of claim 25, wherein each of said pair of conduits include independent distal exits.

30. The applicator of claim 25, wherein said conduit assembly further comprising a first nozzle disposed about a first of said pair of conduits and a second nozzle disposed about a second of said pair of conduits.

31. The applicator of claim 25, wherein said biological adhesive components include a first component and a second component, said first component is a thrombin solution and said second component is a fibrinogen solution.

32. The applicator of claim 31, wherein said biological adhesive comprises a predetermined ratio of said thrombin solution to said fibrinogen solution.

33. The applicator of claim 25, wherein said housing includes a housing head for storing said plurality of reservoirs therein and an elongated body portion extending from said housing head.

34. An applicator for dispensing a first and a second component of a biological adhesive, the applicator comprising:
- a first conduit assembly having a proximal end, an intermediate portion made up at least partially by a first reservoir containing the first component of the biological adhesive, and a distal end;
- a second conduit assembly having a proximal end, an intermediate portion made up at least partially by a second reservoir containing the second component of the biological adhesive, and a distal end;
- an activator assembly in communication with the first and second reservoirs for exerting pressure on the first and second reservoirs for decreasing the volumetric capacity thereof for dispensing the components towards the distal ends of the first and second conduit assemblies; and
- a valve control assembly operatively associated with the first and second conduit assemblies and having a valve operational between a first position and a second position to open and close said first and second conduit assemblies.

35. The applicator of claim 34, wherein the first and second conduit assemblies, the activator assembly and the valve control, assembly are supported within a single housing.

36. An applicator for dispensing a first and second component of a biological adhesive, the applicator comprising:
- a first conduit assembly having a conduit with a proximal end and a distal end;
- a second conduit assembly having a conduit with a proximal end and a distal end;

a reservoir assembly having a first reservoir containing the first component and a second reservoir containing the second component, the first reservoir being in communication with the first conduit and the second reservoir being in communication with the second conduit;

an activator assembly having an activator for imparting pressure to said first and second reservoirs to effect dispensing of said first and second components to said first and second conduits; and a valve assembly having a first valve for opening and closing the proximal ends of said conduits and a second valve for opening and closing the distal ends of said conduits.

37. The applicator of claim 36, wherein the first conduit assembly, the second conduit assembly, the reservoir assembly and the valve assembly are supported within a single housing.

* * * * *